United States Patent [19]  [11] 4,112,216
Maehr  [45] Sep. 5, 1978

[54] CONVERSION OF MOCIMYCIN TO ANTIBIOTIC X-5108 AND INTERMEDIATES

[75] Inventor: Hubert Maehr, Belleville, N.J.

[73] Assignee: Hoffmann-La Roche Inc., Nutley, N.J.

[21] Appl. No.: 749,485

[22] Filed: Dec. 10, 1976

Related U.S. Application Data

[62] Division of Ser. No. 506,156, Sep. 16, 1974, abandoned.

[51] Int. Cl.² .............................................. C07H 3/08
[52] U.S. Cl. ...................................... 536/1; 424/180; 536/17
[58] Field of Search ...................................... 536/1, 17

[56] References Cited

PUBLICATIONS

Berger et al. "The Journal of Antibiotics," vol. XXVI, No. 1, 1973, pp.15-22.
Berger et al. "Chem. Abst." vol. 78, 1973 pp.109, 258(b).

Primary Examiner—Johnnie R. Brown
Attorney, Agent, or Firm—Samuel L. Welt; Jon S. Saxe; Bernard S. Leon

[57] ABSTRACT

The present invention relates to the conversion of the antibiotic mocimycin to the antibiotic known as X-5108 by treating mocimycin with a methylating agent after first protecting the 4-hydroxy functional group of the pyridone moiety, followed by subjecting the protecting group containing ester of X-5108 to mild basic hydrolysis whereby antibiotic X-5108 is obtained.

6 Claims, No Drawings

CONVERSION OF MOCIMYCIN TO ANTIBIOTIC X-5108 AND INTERMEDIATES

This application is a division of Ser. No. 506,156, filed Sept. 16, 1974, now abandoned.

DETAILED DESCRIPTION OF THE INVENTION

Mocimycin is an antibiotic which has been shown to have animal growth promoting properties (Ger. Offen. 2,140,674, C.A. 77 32742 [1972]). It is of the formula

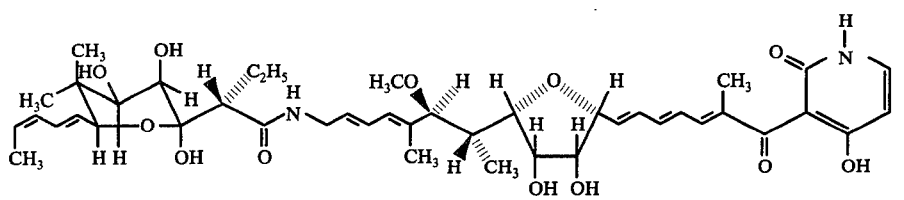

Antibiotic X-5108, has also been shown to have animal growth promotiong properties. (U.S. Pat. No. 3,708,577, J. Antibiotics [Tokyo] 26,15 [1972]) It is of the formula

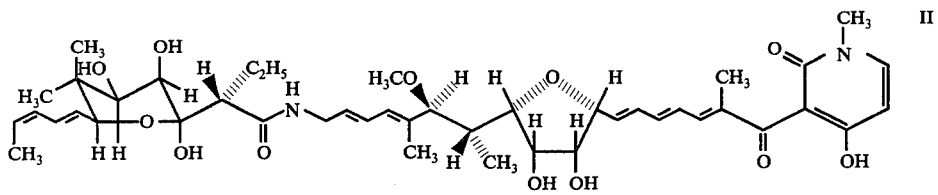

It has been desired to convert mocimycin to X-5108 but the capabilities of affecting this desideratum has not been achieved heretofore due to the pronounced sensitivity of both antibiotic X-5108 and mocimycin toward both acid and basic conditions. Furthermore, because of the reactive groups present in the mocimycin moieties, it has been difficult to effect the desired conversion with the selectivity that is required. It is an object of the present invention to find a convenient and expeditious way of achieving the aforesaid desideratum.

In achieving the objects of the present invention, in the first step, mocimycin, preferably in the form of an alkali metal salt thereof, preferably the sodium salt, is treated with a compound of the formula RCOCO halide (preferably when the halide is chloride) wherein R is selected from a member of the group consisting of lower alkoxy; phenoxy, lower alkyl, phenyl and substituted phenyl, e.g., lower alkyl phenyl (tolyl), halo phenyl, (parachloro phenyl) and the like, whereby a compound of the following formula results

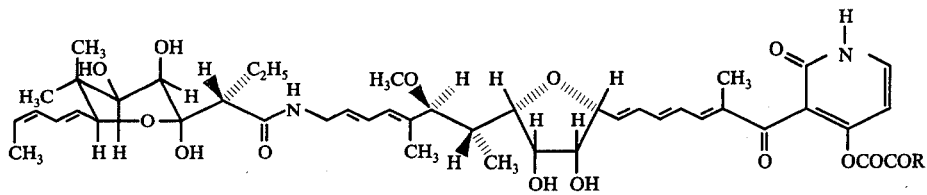

wherein R is as above. Preferably R is phenyl or methyl, most preferably, phenyl.

Preferred compounds of the formula RCOCO halide include phenylglyoxyloxy chloride and methylglyoxyloxy chloride. Halide as used herein includes only the iodides, chlorides and bromides.

The above reaction is preferably effected in the presence of an inert organic solvent which is suitable for the purposes of the present invention. Among the many suitable inert organic solvents, there can be included dimethylformamide, hexamethyl phosphoramide, dimethyl sulfoxide or any other suitable organic solvent.

All that is required of the organic solvent in the first step (as well as in the subsequent steps of the overall process) is that the starting materials be soluble therein and that the solvent does not interfere with the ensuing reaction. While temperature and pressure are not critical to a successful performance of the herein disclosed first step, it is preferred to effect the reaction at a temperature range of from about 20° up to about 70° C, most preferably at about room temperature and atmospheric pressure. The so-obtained compound of the formula III is novel and, hence, constitutes a part of the present invention.

The compounds of the formula III in the second step of the process herein disclosed is converted to the compound of the formula

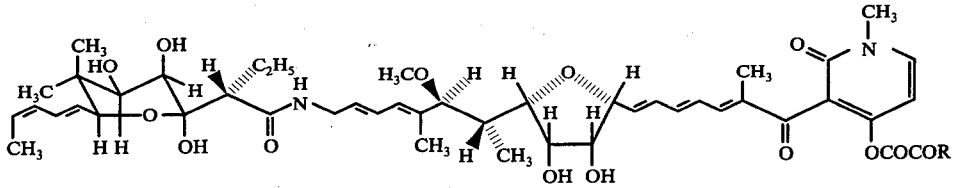

wherein R is as above.
by methylating the compound of the formula III. As suitable methylating agents, there can be utilized a conventional methylating agent, such as a methyl halide, dimethyl sulfate and the like. Preferably, methyl iodide is utilized. Since the use of a methyl halid or dimethyl sulfate in this reaction step would generate a substance of an acidic nature, e.g., HBr, HI, $H_2SO_4$ or $HSO_3OCH_3$ and the molecule of the formula III is sensitive to acidic conditions, it is preferred to carry out the methylating step in the presence of a substance such as an inorganic oxide or hydroxide or an organic amine, which is suitable to neutralize the acid formed during the ensuring reaction.

Thus, in order to control the acidity of the reaction mixture in the second step, the reaction medium should be buffered. The nature of the buffer in the medium is dependent upon the methylating agent utilized. Preferably, there can be utilized as the buffer such substance as silver oxide, sodium bicarbonate and the like, when methyl iodide is utilized in the methylating agent. All that is required of the buffer is that it maintain an environment at a rather constant pH around neutrality.

The conversion of a compound of the formula III to the corresponding compound of the formula IV is suitably affected in the presence of any inert organic solvent. Among the many inert organic solvents that can be utilized, there can be mentioned dimethyl formamide, hexamethyl phosphoramide, dimethyl sulfoxide and the like.

The second step in the reaction sequence is preferably effected at a temperature of from about 20° C to about 70° C, most preferably at about room temperature.

The conversion of a compound IV to the corresponding compound of the formula II is affected under mild conditions, such as by the use of aqueous solutions of a weak base such as pyridine, quinoline and the like. In this last step, the removal of the protecting group on the hydroxyl moiety of the 4-hydroxy function of the pyridone moiety is effected. All that is required to remove the protecting group is that mildly basic conditions be present in the reaction zone which would not effect the sensitive molecule causing extensive side reactions. These mild basic conditions can result from the use of any conventional system which would result in mild basic conditions when added to the reaction medium.

The last step in the process herein described, i.e., the conversion of a compound of the formula IV to the corresponding compound of the formula II, is suitably affected in the presence of an aqueous solvent. Among the many aqueous solvents suitable for the purposes of the present invention, there can be utilized water, mixtures of water and alcohols, e.g., methanol, ethanol, mixtures of water and dimethyl formamide and the like.

The reaction is preferably affected at a temperature of about 20° to about 70° C, most preferably at about room temperature.

The following examples are illustrative but not limited of the present invention. All temperatures are stated in degrees Centigrade.

Tlc described in the following examples was performed with precoated plates (silica gel 60 F-254, Merck, Darmstadt), preparative plates (silica gel P F-254) contained layers of 2 mm thickness, and were developed with systems 1 (chloroform / methanol, 9:1, v/v) or 2 (chloroform, methanol, conc. ammonium hydroxide, 40:10:1, v/v), respectively. All concentrations were carried out under reduced pressure at bath temperatures not exceeding 40°.

EXAMPLE 1

Mocimycin sodium salt (500 mg, 0.6105 mmol) was dissolved in dimethylformamide (5.5 ml) and 0.7 ml of a solution containing approximately 0.7 mmol of phenylglyoxyloyl chloride, prepared by diluting phenylglyoxyloyl chloride (1 g, 5.93 mmol) with benzene (5 ml), was added to the so-obtained solution. The mixture was kept in the dark overnight and was equilibrated with a mixture of water (10 ml) and chloroform (25 ml). The lower phase was washed consecutively with saturated sodium hydrogen carbonate solution (15 ml) and water (15 ml), concentrated to dryness, redissolved in acetone (2 ml) and chromatographed on a column (50 × 475 mm) of Sephadex LH-20, packed in acetone and developed with the same solvent. The column effluent was collected in fractions of 10 ml each, and the composition of the fractions was monitored by tlc (System 1). The phenylglyoxyloyl ester of mocimycin was eluted as the major band ($R_f = 0.23$) essentially free of minor impurities with $R_f$— values of 0.12, 0.16 (unreacted mocimycin), 0.18, 0.26 and 0.30. The fractions were pooled and concentrated to dryness to yield 182 mg of the phenylglyoxyloyl ester of the mocimycin (0.196 mmol, 32%) as amorphous, yellow powder with an nmr spectrum sililar to that of mocimycin but with addtional signals characteristic for the phenylglyoxloyl group, $TMS^{CDCl_3}$ 3.17 (s, $OCH_3$), 7.47 (m, 3H of phenyl group overlapping with H-6 of pyridone moiety) and 7.95 (d, 2H of phenyl group, $J_o = 8Hz$).

EXAMPLE 2

Mocimycin (250 mg, 75% purity, 0.235g) was dissolved in anhydrous pyridine (2.5 ml). the solution was cooled in an ice-bath and 0.6 ml of the phenylglyoxyloyl chloride solution prepared as described in Example 1 was added under stirring. After 5 min, the solution was equilibrated with a mixture of chloroform (25 ml), saturated sodium hydrogen carbonate solution (15 ml) and crushed ice. The chloroform phase was washed twice with ice-cold water, concentrated to dryness, the residue was dissolved in acetone and chromatographed as described previously, to yield 115 mg of the phenylglyoxyloyl ester of mocimycin III (0.124 mmol, 53%).

EXAMPLE 3

A mixture of the phenylglyoxyloyl ester of mocimycin (182 mg, 0.196 mmol), siliver oxide (approx. 100 mg), dimethyl formamide (9 ml) and methyl iodide (0.37 ml) was shaken for 70 min at room temperature. The suspension was filtered and the filtrate was equilibrated with ethyl acetate (25 ml) and water (50 ml). The ethyl acetate phase was filtered, concentrated to a thin syrup, diluted with acetone (2 ml) and chromatographed on a column (25 × 450 mm) of Sephadex LH-20 packed in acetone and developed with the same solvent. Fractions containing 5 ml each were collected and analyzed by tlc (System I), fractions containing the major band ($R_f$ = 0.30) were largely free of impurities which were eluted immediately before ($R_f$ = 0.33, 0.39, 0.46) and after ($R_f$ = 0.16, 0.20, 0.25) the major band. Concentration of the pooled fractions afforded 103 mg of the phenylglyoxyloyl ester of antibiotic X-5108 as yellow, amorphous powder (0.109 mmol, 55.6%). The nmr spectrum of the so-obtained product is very similar to that of the phenylglyoxyloyl ester of mocimycin with the exception of a signal for an N-methyl group, $\tau_{TMS}^{CDCl_3}$ 3.17 (s, OCH$_3$), 3.58 (s, N-CH$_3$), 7.39 (d, H-6 of pyridone moiety, J = 8Hz) overlapping with 7.46 (m, 3H of phenyl group) and 7.96 (d), 2H of phenyl group, $J_o$ = 8Hz).

EXAMPLE 4

A solution of the phenylglyoxyloyl ester of antibiotic X-5108 (103 mg, 0.109 mmol) in pyridine (2.5 ml) and water (2.5 ml) was kept at room temperature for 7 days, concentrated to a thin syrup and redissolved in chloroform. This solution was washed twice with saturated sodium hydrogen carbonate solution, once with water, concentrated and applied to two preparative tlc plates. The plates were developed with system 2, the major band ($R_f$ = 0.13) was eluted with chloroform/methanol, 4:1. The antibiotic X-5108 ammonium salt (37 mg, 0.045 mmol, 41%) could be converted to the free acid by equilibrating with primary sodium phosphate solution and methylene chloride, followed by washing ot the methylene chloride solution with water, drying and concentration to dryness.

I claim:

1. A compound of the formula

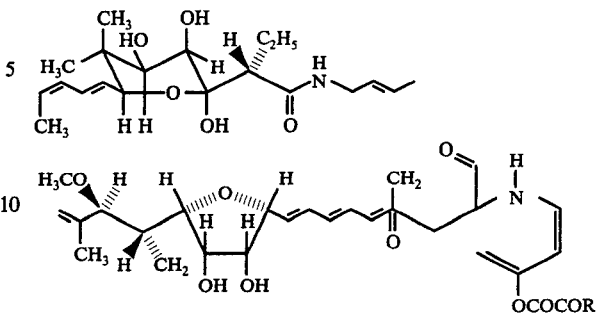

wherein R is selected from the group consisting of lower alkoxy, lower alkyl, phenoxy, phenyl and lower alkyl phenyl and halo phenyl.

2. A compound as defined in claim 1 wherein R is phenyl.

3. A compound as defined in claim 1 wherein R is methyl.

4. A compound of the formula

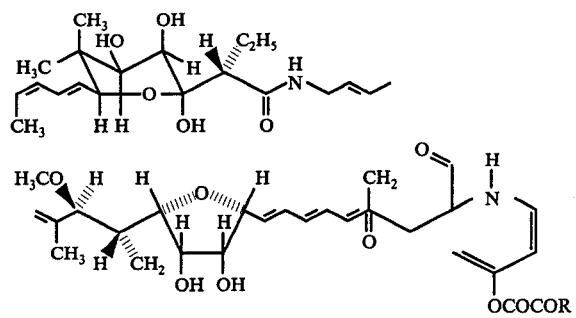

wherein R is selected from the group consisting of lower alkoxy, phenoxy, lower alkyl, phenyl and lower alkyl phenyl and halo phenyl.

5. A compound as defined in claim 4 wherein R is phenyl.

6. A compound as defined in claim 4 wherein R is methyl.

* * * * *